United States Patent
Eker et al.

(10) Patent No.: US 11,229,538 B2
(45) Date of Patent: Jan. 25, 2022

(54) DELIVERY SYSTEM FOR A BIFURCATED STENT

(71) Applicants: Omer Faruk Eker, Lyons (FR); Kamil Jerzy Chodzynski, Mons (BE)

(72) Inventors: Omer Faruk Eker, Lyons (FR); Kamil Jerzy Chodzynski, Mons (BE)

(*) Notice: Subject to any disclaimer, the term of this patent is extended or adjusted under 35 U.S.C. 154(b) by 140 days.

(21) Appl. No.: 16/478,923

(22) PCT Filed: Jan. 10, 2018

(86) PCT No.: PCT/EP2018/050554
§ 371 (c)(1),
(2) Date: Jul. 18, 2019

(87) PCT Pub. No.: WO2018/134097
PCT Pub. Date: Jul. 26, 2018

(65) Prior Publication Data
US 2019/0380852 A1    Dec. 19, 2019

(30) Foreign Application Priority Data

Jan. 19, 2017 (EP) .................................. 17290006
Jan. 25, 2017 (BE) .................................. 20175043

(51) Int. Cl.
*A61F 2/954* (2013.01)
*A61F 2/07* (2013.01)
(Continued)

(52) U.S. Cl.
CPC .............. *A61F 2/954* (2013.01); *A61F 2/07* (2013.01); *A61F 2/90* (2013.01); *A61F 2/97* (2013.01);
(Continued)

(58) Field of Classification Search
CPC ...... A61F 2002/065; A61F 2/954; A61F 2/07; A61F 2/90; A61F 2/97; A61F 2/9522;
(Continued)

(56) References Cited

U.S. PATENT DOCUMENTS 5,755,771 A * 5/1998 Penn ..................... A61F 2/91
623/1.15
6,514,281 B1 * 2/2003 Blaeser ................. A61F 2/954
623/1.12
(Continued)

FOREIGN PATENT DOCUMENTS

EP    2 731 558       5/2014
JP    2003-500105     1/2003
(Continued)

OTHER PUBLICATIONS

International Search Report for PCT/EP2018/050554 dated Apr. 9, 2018, 4 pages.
(Continued)

*Primary Examiner* — George J Ulsh
*Assistant Examiner* — Andrew P. Restaino
(74) *Attorney, Agent, or Firm* — Nixon & Vanderhye P.C.

(57) ABSTRACT

A delivery system (100) for a bifurcated stent (200) is described having a stem (226) and a pair of arms (220, 222), comprising a delivery catheter (110) comprising an elongated first tube (102) having a proximal end (20) and a distal end (30) and a bifurcated part (114) at the distal end (30) configured to accommodate the arms (220, 222), wherein a longitudinal slit (140) disposed on the bifurcated part (114) is configured for releasable passage of the bifurcated stent (200) therethrough. A method for delivery of the bifurcated stent to a site of treatment using the delivery system (100) is also described.

20 Claims, 9 Drawing Sheets

(51) Int. Cl.
- *A61F 2/90* (2013.01)
- *A61F 2/97* (2013.01)
- *A61F 2/966* (2013.01)
- *A61F 2/06* (2013.01)
- *A61F 2/95* (2013.01)

(52) U.S. Cl.
CPC ............ *A61F 2/9522* (2020.05); *A61F 2/966* (2013.01); *A61F 2002/065* (2013.01); *A61F 2002/9665* (2013.01); *A61F 2210/0014* (2013.01); *A61F 2250/0067* (2013.01)

(58) Field of Classification Search
CPC ............ A61F 2/966; A61F 2002/9665; A61F 2210/0014; A61F 2250/0067; A61F 2/91
See application file for complete search history.

(56) References Cited

U.S. PATENT DOCUMENTS

| | | |
|---|---|---|
| 2005/0209677 A1 | 9/2005 | Shaked |
| 2008/0262592 A1* | 10/2008 | Jordan ................. A61F 2/95 623/1.11 |
| 2009/0132019 A1 | 5/2009 | Duffy et al. |
| 2011/0208292 A1 | 8/2011 | Van Oepen et al. |
| 2011/0313505 A1* | 12/2011 | McHugo ................. A61F 2/966 623/1.12 |
| 2013/0211501 A1 | 8/2013 | Buckley et al. |
| 2014/0148891 A1* | 5/2014 | Johnson ................. A61F 2/97 623/1.11 |
| 2014/0236123 A1* | 8/2014 | Birmingham ..... A61M 39/0247 604/525 |
| 2016/0206203 A1* | 7/2016 | Yu ......................... G06T 11/008 |
| 2016/0346104 A1* | 12/2016 | Kramer ................. A61F 2/90 |

FOREIGN PATENT DOCUMENTS

| | | |
|---|---|---|
| JP | 2008-520360 | 6/2008 |
| WO | 00/71059 | 11/2000 |
| WO | 2006/055692 | 5/2006 |

OTHER PUBLICATIONS

Written Opinion of the ISA for PCT/EP2018/050554 dated Apr. 9, 2018, 6 pages.
Japanese Patent Office Action dated Jul. 28, 201, in related Japanese Patent Application No. 2019-560463.
EP Office Action cited in Application No. 18 701 270.3 dated Aug. 9, 2021, 7 pages.

* cited by examiner

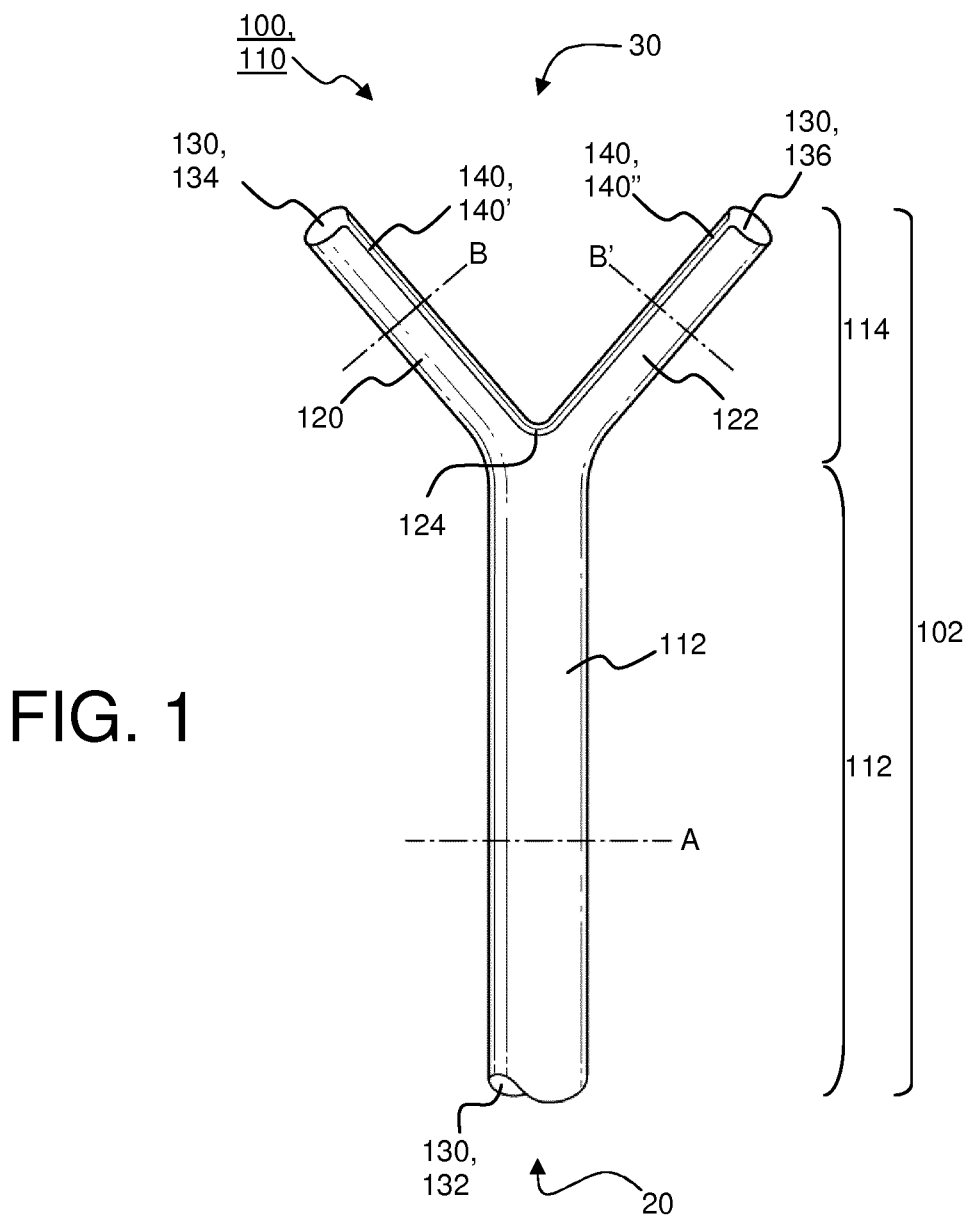
FIG. 1
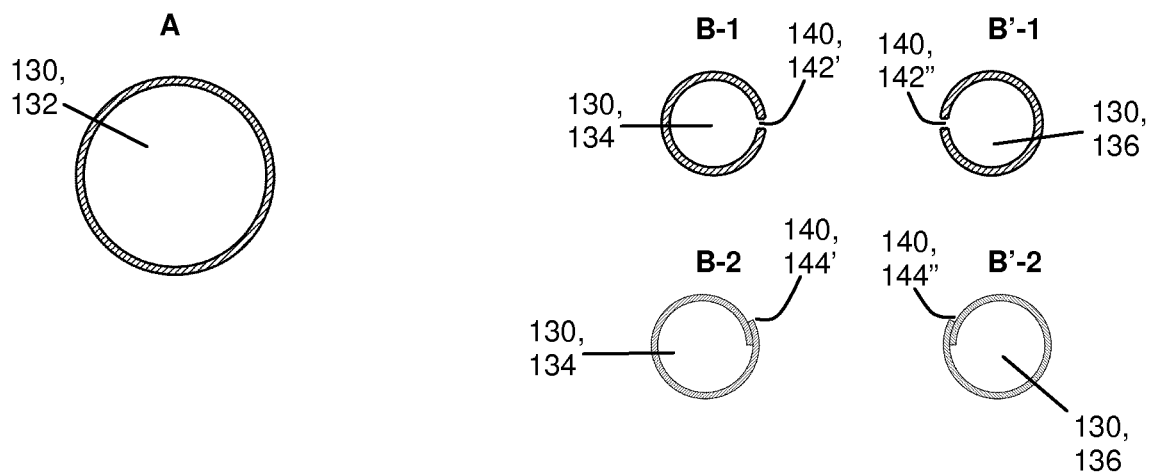

DELIVERY SYSTEM FOR A BIFURCATED STENT

This application is the U.S. national phase of International Application No. PCT/EP2018/050554 filed Jan. 10, 2018 which designated the U.S. and claims priority to EP Patent Application No. 17290006.0 filed Jan. 19, 2017 and BE Patent Application No. 20175043 filed Jan. 25, 2017, the entire contents of each of which are hereby incorporated by reference.

FIELD OF THE INVENTION

Delivery system for a bifurcated stent and method for treating an artery (e.g. aneurysm or occlusion) located at the bifurcation of an artery are described herein. The system and method may be implemented for bifurcation aneurysms or occlusions located intracranially or extracranially (i.e., aortic or peripheral aneurysms).

BACKGROUND TO THE INVENTION

An intracranial aneurysm is a saccular, or more rarely a fusiform, dilatation of a cerebral artery due histological structural changes in the arterial wall. It is responsible for a wall weakness which is at risk of rupture if untreated and hence of intracranial bleeding (subarachnoid hemorrhage and/or intra parenchymal). Amongst younger populations, intracranial aneurysmal disease represents the most prevalent predisposition to a fatal risk with an estimated incidence of 5-7 cases per 100,000 persons per year and prevalence between 2-5%. It is the leading cause of hemorrhagic stroke and is responsible for a reduction in life expectancy and for potentially severe disabilities affecting quality of life. The mortality rate associated with subarachnoid hemorrhage secondary to ruptured intracranial aneurysm is estimated at 45-50% at thirty days. The associated morbidity is estimated at 25-30%, with dependence in nearly 30% of patients at one year despite appropriate and early treatment. The risk of rupture of unruptured intracranial aneurysm is difficult to estimate and varies between 0.4% and 17.8% at five years. It is increased by the following factors: age, gender, hypertension, smoking, aneurysm size and location in posterior circulation. Finally, the aneurysmal rupture and its complications have a significant economic impact in terms of costs related to the management of the acute phase, the neurological deficits and/or subsequent dependence. In the Europe alone, thirty-five to thirty-seven million people may have intracranial aneurysms. In France alone, six thousand intracranial hemorrhages secondary to ruptured intracranial aneurysms occur each year.

The main goal of intracranial aneurysm treatment, whatever the chosen method, is to exclude the malformative out-pouching from the blood circulation. Most of the current practices for treating intracranial aneurysms are based on endovascular catheter-based approaches mainly represented by the aneurysm's filling with a filler material (the so-called "coiling" technique with platinum coils and/or cellulose acetate polymer). The filling material deployment within the aneurysm may be associated to the inflation of a balloon within the arterial lumen during the filling material deployment (called the "balloon remodeling method") or to the deployment of stent within the artery covering aneurysm's neck (called the "stent assisted coiling method") in order to prevent its protrusion within the artery. It results in a thrombus formation inside the aneurysm and its exclusion from the blood circulation. These techniques have become very quickly the gold standard methods for intracranial treatment. The historical surgical clipping approach consists in the placement of an aneurysm clip across the aneurysm to prevent blood flow into the aneurysm. This technique is more invasive and less and less carried out because of its high risk, especially for elderly or medical complicated patients.

Described methods above are related to remain device permanently in the body for aneurysm treatment or related to its transitory deployment in the arterial bifurcation lumen and then its retrieval for the treatment or arterial occlusion. For the first purpose, the latest invention of biodegradable polymers may solve this problem and device will be able to be removed from the body by dissolving biopolymers itself by time or using chemicals components. For the last purpose, the stent may be deployed and remain permanently in the body in case of arterial stenosis and therefore it presents the same material characteristics described above apart from its design (laser cut instead of braided mesh).

Despite the significant advance allowed and the paradigm shift created in the management of intracranial aneurysms by endovascular techniques, bifurcation aneurysms and especially those presenting a large neck or a neck encompassing one or both of the division branches remain challenging for their treatment. Stenting techniques represent an alternative for those aneurysms. Presently, many strategies are employed to treat intracranial bifurcation aneurysms with currently available stent designs (either laser cut or braided stents) including: stent assisted coiling, Y-stent, T-Stent or Crush-stent techniques. With stents, one common approach is to place the stent (either laser cut or braided stent) in the main artery and one of its branch (more commonly the biggest branch or the branch more affected by the aneurysm) before (jailing method) or after coiling the aneurysm sac. If the first deployed stent is not efficient enough to prevent the coil protrusion into the arterial lumen, a second stent is deployed within the first stent and the second branch (called Y-stent technique). This latter technique may be used as first option according to the arterial anatomy and the access difficulties. However, with these methods the amount of material within the arterial lumen and precisely across the arterial branche(s) are source of thromboembolic complications, increased in Y-stent, T-Stent and Crush-stent techniques. Recently, flow diversion technique based on the deployment of flow diverter stent within the parent artery and flow disruption technique based on the deployment of an intrasaccular flow disruption device within the aneurysm became also options for those challenging aneurysms. Because of the higher amount of material in their design, the flow diverter stents are at higher risk of thromboembolic complications. Additionally, in arterial bifurcation the deployed flow diverter stent within the arterial lumen covers not only the side perforators but also the division branch which may compromise its patency at long term. The flow disruption device method consists of a frame, based on the same braided meshes as braided stents, that is deployed into the aneurysm sac in order to fill in it, thereafter to stop the flow within the aneurysm sac and to promote the intrasaccular thrombosis. This approach is limited either by the incomplete occlusion of the aneurysm at its neck or the bulging of the frame into the arterial lumen that imposes a secondary rescue stenting. These limitations are due to the design of the frame which in most of cases despite its compliance does not enable the perfect conformation of the device to the aneurysm neck and wall.

It is an aim of the invention to overcome problems encountered in the art. It is a further aim to provide new therapies for certain type of intracranial aneurysms located at the bifurcation of an artery for which the present day therapies are widely regarded as inadequate.

SUMMARY

Described herein is a delivery system (100) for a bifurcated stent (200) having a stem (226) and a pair of arms (220, 222), comprising a delivery catheter (110) comprising an elongated first tube (102) having a proximal end (20) and a distal end (30) and a bifurcated part (114) at the distal end (30) configured to accommodate the arms (220, 222), wherein a longitudinal slit (140) disposed on the bifurcated part (114) is configured for releasable passage of the bifurcated stent (200) therethrough.

The longitudinal slit may extend from a first limb (120) to a second limb (122) of the bifurcated part (114).

The bifurcated part (114) of the first tube (102) may comprise a first (120) and second (122) limb each configured for passage through a branch (422, 424) of a bifurcated bodily vessel.

The first (120) and second (122) limbs may each be configured to compress radially the bifurcated stent (200).

The delivery system (100) may further comprise an access catheter (300) comprising an elongated second tube (302) having a proximal end (20) and a distal end (30) provided with a second lumen (330) adapted to slidably accommodate the first tube (102), and configured to control a gradual opening or folding of the bifurcated part (114) of the first tube (102) responsive to slidable relative displacement of the first (102) and second (302) tubes.

The delivery catheter (110) may be configured for an over-the-wire or rapid exchange mode of operation.

The delivery system (100) may further comprise the bifurcated stent (200) that is self-expanding. The bifurcated stent (200) may be provided with an elutable active pharmaceutical ingredient, optionally having an antithrombotic property, or anticoagulant property, or endothelisation property, or that is a stimulator of cell migration, or a stimulator of cell growth. The bifurcated stent (200) may be prepared by laser cutting or braiding.

The delivery system (100) may further comprise a pusher (500) comprising an elongated flexible rod (510) having a proximal (20) and distal (30) end, and a capture element (520) at the distal (30) end for releasable attachment to the bifurcated stent (200) at its proximal end (20) which capture element (520) is radially self-expanding to adopt an open or folded configuration, wherein the folded configuration is configured for passage within the first lumen (230) of the first tube (102) and the peripheral edges of the capture element (520) are closer together to grip the proximal end (20) of the bifurcated stent (200), and wherein the open configuration is configured for release of the bifurcated stent (200).

The delivery system (100) may further comprise a loader (600) for loading of the bifurcated stent (200) into the delivery catheter (110) comprising an elongated third tube (602) having a proximal end (20) and a distal end (30) provided with a third lumen (630) adapted to slidably accommodate the bifurcated stent (200) in the folded configuration, wherein the distal end (30) of the third tube (602) is configured to couple with the proximal terminal end of the delivery catheter (110) such that the first (130) and third (630) lumens are connected to form a continuous passage for advancement of the bifurcated stent (200) in the folded state from the loader (600) to the delivery catheter (110).

Described herein is a kit comprising the delivery catheter (110) as defined herein, and one or more of:
  an access catheter (300) as defined herein,
  a bifurcated stent (200) as defined herein,
  a pusher (500) as defined herein,
  a loader (600) as defined herein, and
  one or more guidewires.

Described herein is a method for delivery of a bifurcated stent to a site of treatment using the delivery system (100) as defined herein comprising the steps:
  advancing intravascularly the delivery catheter (110) loaded with the bifurcated stent (200) to the site of treatment through the access catheter (300),
  opening gradually the delivery catheter (110) by withdrawal of the access catheter (300), and deploying the bifurcated stent (200) through the slit (140) by withdrawal of the delivery catheter (110).

The treatment may be of an arterial aneurism or arterial occlusion.

FIGURE LEGENDS

FIG. 1 Schematic view of a delivery catheter as described herein. Panels A, B, and B' show transverse cross-sectional view through limbs at planes B and B', and main part at plane A respectively. Panels B-1 and B'-1 show a slit with abutting edges, and Panels B-2 and B'-2 a slit with overlapping edges.

FIG. 2 Schematic view of a bifurcated stent as described herein.

FIG. 3 Panels A to C Sequence of gradual unfolding (opening) the delivery catheter by slidable actuation of the access catheter.

FIG. 4 Panels A to D Sequence of delivering and unfolding (opening) the delivery catheter at the site of treatment, and deployment of the bifurcated stent.

Figure 9:
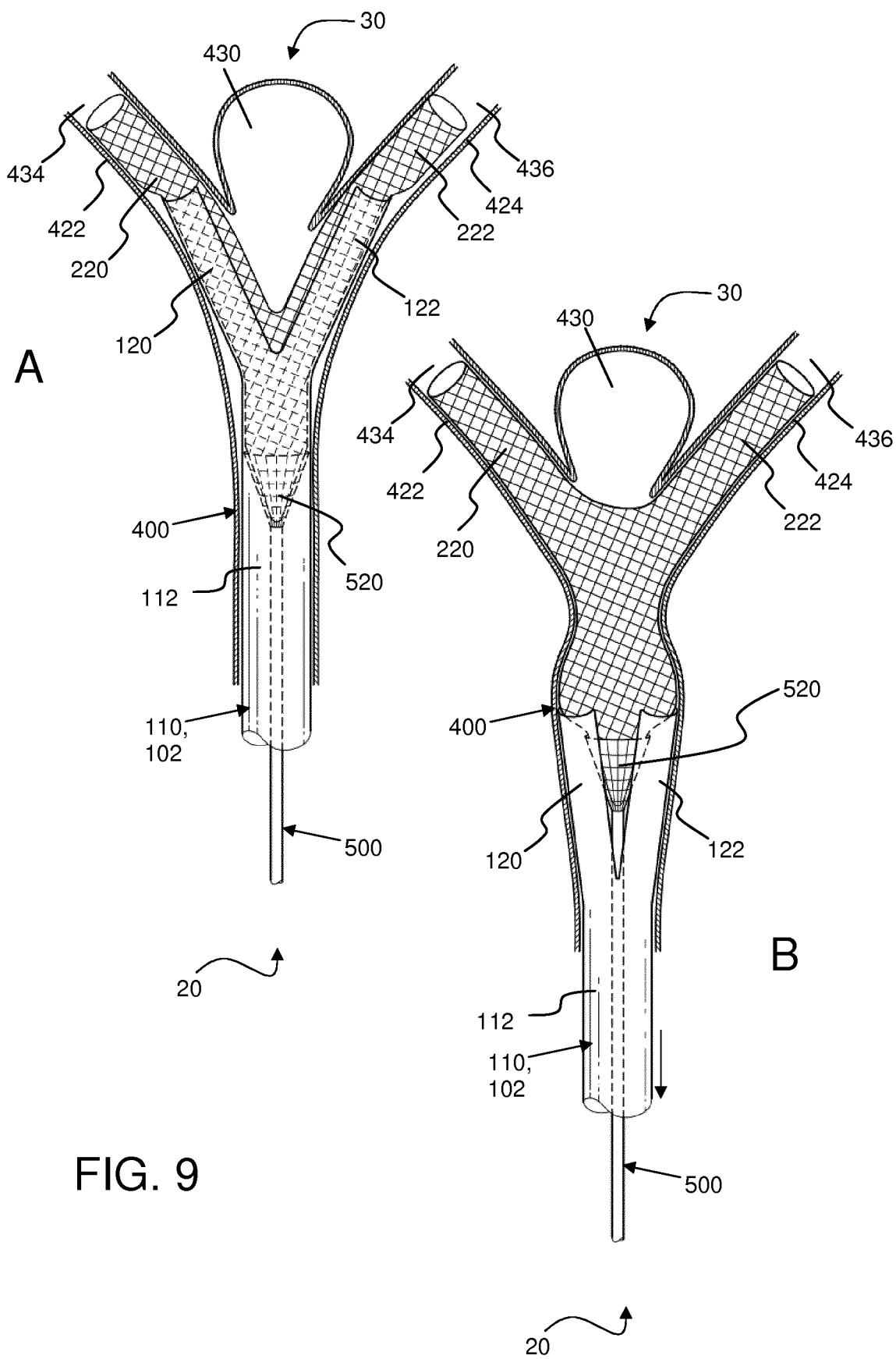

FIG. 9 Panels A and B depict a sequence of deployment of the bifurcated stent using the pusher.

Figure 10:
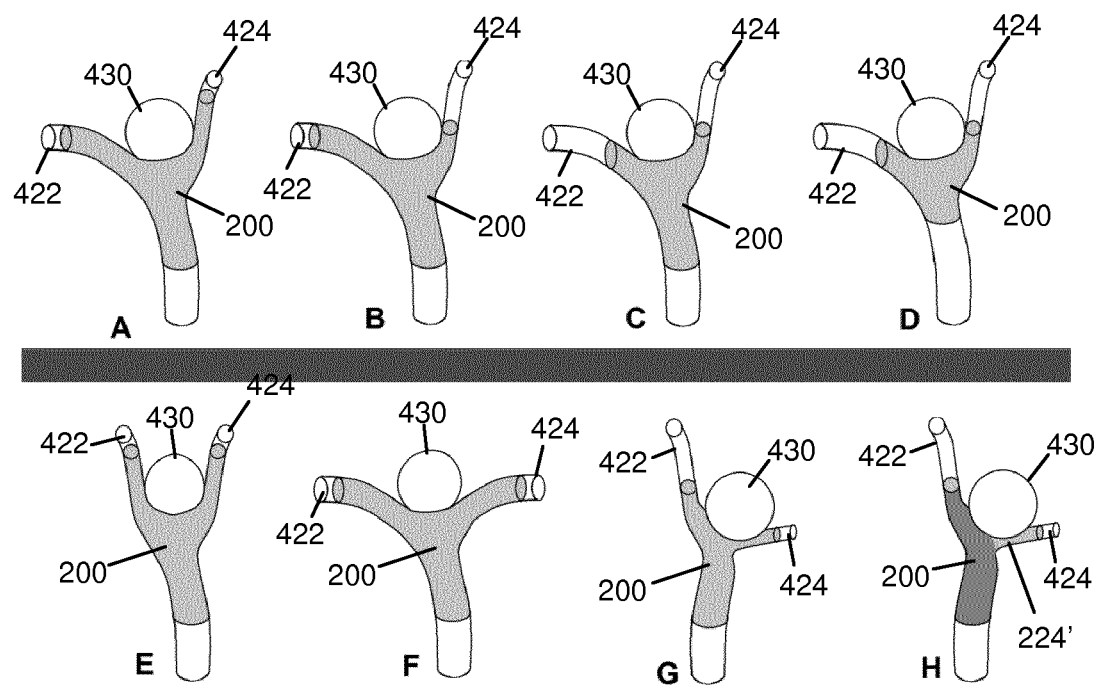

FIG. 10 Panels A to H depict different bifurcated stent configurations.

DETAILED DESCRIPTION OF INVENTION

Before the present system and method of the invention are described, it is to be understood that this invention is not limited to particular systems and methods or combinations described, since such systems and methods and combinations may, of course, vary. It is also to be understood that the terminology used herein is not intended to be limiting, since the scope of the present invention will be limited only by the appended claims.

As used herein, the singular forms "a", "an", and "the" include both singular and plural referents unless the context clearly dictates otherwise.

The terms "comprising", "comprises" and "comprised of" as used herein are synonymous with "including", "includes" or "containing", "contains", and are inclusive or open-ended and do not exclude additional, non-recited members, elements or method steps. It will be appreciated that the terms "comprising", "comprises" and "comprised of" as used herein comprise the terms "consisting of", "consists" and "consists of".

The recitation of numerical ranges by endpoints includes all numbers and fractions subsumed within the respective ranges, as well as the recited endpoints.

The term "about" or "approximately" where used herein when referring to a measurable value such as a parameter, an amount, a temporal duration, and the like, is meant to encompass variations of +/−10% or less, preferably +/−5% or less, more preferably +/−1% or less, and still more preferably +/−0.1% or less of and from the specified value, insofar such variations are appropriate to perform in the disclosed invention. It is to be understood that the value to which the modifier "about" or "approximately" refers is itself also specifically, and preferably, disclosed.

Whereas the terms "one or more" or "at least one" where used herein, such as one or more or at least one member(s) of a group of members, is clear per se, by means of further exemplification, the term encompasses inter alia a reference to any one of said members, or to any two or more of said members, such as, e.g., any ≥3, ≥4, ≥5, ≥6 or etc. of said members, and up to all said members.

All references cited in the present specification are hereby incorporated by reference in their entirety. In particular, the teachings of all references herein specifically referred to are incorporated by reference.

Unless otherwise defined, all terms used in disclosing the invention, including technical and scientific terms, have the meaning as commonly understood by one of ordinary skill in the art to which this invention belongs. By means of further guidance, term definitions are included to better appreciate the teaching of the present invention.

In the following passages, different aspects of the invention are defined in more detail. Each aspect so defined may be combined with any other aspect or aspects unless clearly indicated to the contrary. In particular, any feature indicated as being preferred or advantageous may be combined with any other feature or features indicated as being preferred or advantageous.

Reference throughout this specification to "one embodiment" or "an embodiment" means that a particular feature, structure or characteristic described in connection with the embodiment is included in at least one embodiment of the present invention. Thus, appearances of the phrases "in one embodiment" or "in an embodiment" in various places throughout this specification are not necessarily all referring to the same embodiment, but may. Furthermore, the particular features, structures or characteristics may be combined in any suitable manner, as would be apparent to a person skilled in the art from this disclosure, in one or more embodiments. Furthermore, while some embodiments described herein include some but not other features included in other embodiments, combinations of features of different embodiments are meant to be within the scope of the invention, and form different embodiments, as would be understood by those in the art. For example, in the appended claims, any of the claimed embodiments can be used in any combination.

In the present description of the invention, reference is made to the accompanying drawings that form a part hereof, and in which are shown by way of illustration only of specific embodiments in which the invention may be practiced. Parenthesized or emboldened reference numerals affixed to respective elements merely exemplify the elements by way of example, with which it is not intended to limit the respective elements. It is to be understood that other embodiments may be utilised and structural or logical changes may be made without departing from the scope of the present invention. The following detailed description, therefore, is not to be taken in a limiting sense, and the scope of the present invention is defined by the appended claims.

The terms "distal", "distally" or "distal to" and "proximal", "proximally" or "proximal to" are used throughout the specification, and are terms generally understood in the field to mean towards (proximal) or away (distal) from the surgeon's side of the apparatus. Thus, "proximal", "proximally" or "proximal to" means towards the surgeon's side and, therefore, away from the patient's side. Conversely, "distal", "distally" or "distal to" means towards the patient's side and, therefore, away from the surgeon's side.

A first aspect relates to a delivery system (100) for a bifurcated stent (200) having a stem (226) and a pair of arms (220, 222) comprising:

a delivery catheter (110) comprising an elongated first tube (102) having a proximal end (20) and a distal end (30) and a bifurcated part (114) at the distal end (30) configured to accommodate the arms (220, 222), wherein a longitudinal slit (140) disposed on the bifurcated part (114) is configured for releasable passage of the bifurcated stent (200) therethrough.

Used in the treatment of a bodily vessel, in particular of a vascular vessel such as an artery.

Figure 2:
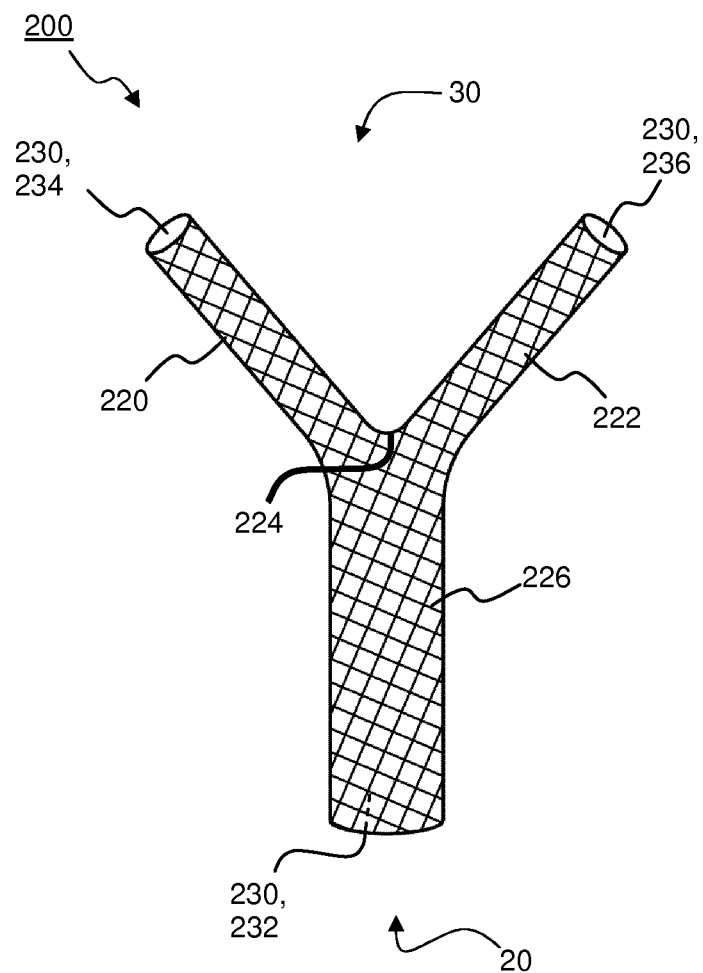

The bifurcated stent (200) is a stent having a proximal end (20) and a distal end (30), comprising a stem part (226) at the proximal end (20) bifurcating into a pair of arms (220, 222) at the distal end, as illustrated, for instance, in FIG. 2. A stent lumen (230) extends from the proximal end (232) of the stem to the distal end of each arm (234, 236). The ends of the bifurcated stent (200) are preferably open for the passage of bodily fluid in situ. The bifurcated stent (200) is flexible and may be compliant.

The bifurcated stent (200) may be used for the treatment of an aneurysm located at the bifurcation of a bodily vessel, the bodily vessel having a wall and a bifurcation into two division branches. The aneurysm having a neck may be located at the arterial bifurcation communicating with the bodily vessel lumen at the bifurcation, and communicating or not with predominantly one or both division branches. The aneurysm may encompass one or both the division branches.

The bifurcated stent (200) may be used for the treatment of an occlusion to vessel wall. The occlusion may encompass one or both branches.

According to one aspect the occlusive material (e.g. clot, thrombus, embolus) is penetrated by an arm of the bifurcated stent (200), and the bifurcated stent (200) is withdrawn thereby removing at least part of the occlusive material from the site of treatment.

According to another aspect the occlusion is opened by an inflatable balloon. The opening may be prior to deployment of the bifurcated stent (200), or may be simultaneously with expansion of the bifurcated stent (200). Where it is simultaneous, the delivery catheter may accommodate an additional tube or lumen for inflation of the inflatable balloon; and the bifurcated stent (200) balloon-expandable (non-self expanding).

The bifurcated stent (200) may adopt an expanded or compressed configuration. The compressed configuration is for passage within a delivery catheter (110) through a bodily vessel wherein the stent arms (220, 222) and stem (226) have a narrowed transverse cross-sectional profile. The expanded configuration is adopted after deployment; the stent arms and stem have an increased transverse cross-sectional profile. The expanded configuration contacts the inner lumen walls of the bodily vessel. It is understood that in situ, the bifurcated stent (200) may not be fully expanded; it is generally disposed in a transition state between fully expanded and fully compressed wherein the bifurcated stent (200) applies a radial force to the vessel wall. Generally the expanded configuration when discussed herein may be also taken to mean the aforementioned transition state without full expansion.

The bifurcated stent is preferably self-expanding. It is preferably biased in the expanded configuration; no application of force is required to maintain the expanded configuration. When an external radial force is applied, the bifurcated stent arms (220, 222) and stem (226) may each be radially compressed, thereby reducing the transverse cross-sectional profile (e.g. diameter) of the stent arms and stem in the compressed configuration. The self-expanding bifurcated stent may be retained in the compressed configuration within the first lumen (130) of the first tube (102) as described later below. The bifurcated stent in the compressed configuration is exemplified in FIG. 4 Panel A, and in the expanded configuration in FIG. 4 Panel D. The self-expanding stent is preferably formed from a shape memory material such NiTinol, chrome-cobalt alloy, or a biodegradable material.

According to one aspect, the bifurcated stent may be balloon-expandable (non-self-expanding). A balloon-expandable bifurcated stent may be mounted on a balloon for delivery to the site of treatment and to actuate expansion.

The bifurcated stent (200) may further adopt an open or folded configuration. The folded configuration is for passage within an access catheter (300) through a bodily vessel wherein the stent arms (220, 222) are closer together, typically having an essentially "I"-shaped profile. The open configuration is adopted after deployment within the bodily vessel, the stent arms (220, 222) disposed wider apart, typically having an essentially "Y"-shaped profile.

The bifurcated stent (200) may be compliant and biased in the open ("Y"-shaped) configuration. Upon the application of force the stent transitions into the folded configuration. With the release of the force, the bifurcated stent (200) returns to the open ("Y"-shaped) configuration. The bifurcated stent (200) may be retained in the closed ("I"-shaped profile) configuration within the second lumen (330) of the second tube (302) as described later below. The bifurcated stent (200) in the closed configuration is exemplified in FIG. 4 Panel A, and in the open configuration in FIG. 4 Panel B.

A bifurcated stent wall extends along the stem (226) at the proximal end (20) to each of the arms (220, 222) at the distal end (30) defining a stent lumen. The stent lumen (230) is dimensioned in the expanded configuration for the flow of bodily fluid e.g. blood. The stent lumen may be dimensioned in the compressed configuration for the slidable passage of one or more, preferably two, guidewires. More in particular, the stent lumen (232) in the stem part (226) may be dimensioned in the compressed configuration for the slidable passage of two guidewires, and the stent lumen (234, 236) of the arms (220, 222) may be dimensioned in the compressed configuration for the slidable passage of one guidewire each.

The bifurcated stent arms may be of equal length in the unfolded condition. Alternatively, the bifurcated stent arms may be of unequal length in the unfolded condition. Exemplary configurations of bifurcated stent are shown in FIG. 10, Panels A to G.

The stent wall may or may not be permeable to blood flow. It may present a variable porosity along the length of the stent allowing to use the stent as a scaffold for the filling of the aneurysm (e.g., as stent-assisted coiling technique) or as a flow diverter stent. The porosity may vary according to its compression or stretching during its deployment. An exemplary configurations of bifurcated stent having an arm (224') of variable porosity is shown in FIG. 10, Panel H.

The bifurcated stent (200) may or may not be drug-eluting. According to one aspect, the bifurcated stent is provided with an active pharmaceutical ingredient having an antithrombotic property, or anticoagulant property, or endothelisation property, or that is a stimulator of cell migration, or a stimulator of cell growth. The active pharmaceutical ingredient may be provided on an inner surface and/or an outer surface of the bifurcated stent (200).

A different active pharmaceutical ingredient may be provided on an inner surface compared with an outer surface of the bifurcated stent (200). For instance, an inner surface may be provided with an active pharmaceutical ingredient that promotes patency of the vessel, while an outer surface may be provided with an active pharmaceutical ingredient that promotes thrombosis, coagulation or healing.

According to one aspect, the bifurcated stent is provided with an active pharmaceutical ingredients at its inner surface having an antithrombotic property, or anticoagulant property, or pro-endothelisation property, or that is a stimulator of cell migration, or a stimulator of cell growth, and at its outer surface having a prothrombotic property, or procoagulant property, or pro-endothelisation property, or that is a stimulator of cell migration, or a stimulator of cell growth.

The bifurcated stent (200) may be manufactured by braiding wires or by laser-cutting techniques as is known in the art. For aneurysm treatment, the stent allows for blood flow redirecting (i.e., diversion) and therefore promotes thrombus formation inside bifurcation aneurysms and their occlusion.

Typically, the delivery catheter (110) comprises an elongated first tube (102) having a proximal end (20) and a distal end (30) and bifurcated part (114) at the distal end (30). The bifurcated part (114) comprises a first limb (120) and a second limb (122). The first (120) and second (122) limbs are mutually connected at a bifurcation point (124) and to the remainder of the first tube (102) proximal to the bifurcation point (124). The remainder of the first tube (102) proximal to the bifurcated part (114) is also known as the main part (112) of the first tube (102).

The first tube (102) is disposed with a first lumen (130). The first lumen (130) is in fluid connection with a proximal end (20) of the main part (112) of the first tube (102) and bifurcates (134, 136) at the distal end (30), corresponding to the bifurcation of the first tube (120). The bifurcated part (114) of the first lumen (134, 136) is configured to accommodate the arms (220, 222) of the bifurcated stent (200). The main part (112) of the first lumen (232), is configured to accommodate the stem (226) of the bifurcated stent (200), in particular, immediate distal to the bifurcation point (124). The main part of the first lumen (232) may be further configured for the passage of one or more guidewires, preferably two guidewires, one for each of the bifurcated limbs (120, 122). The ends of the delivery catheter (110) are preferably open for the passage of the one or more guidewires.

The bifurcated part (114) of the first tube (102) accommodates the arms (220, 222) of the bifurcated stent (200). Where the bifurcated stent (200) is self-expanding, the first tube (102) is adapted to maintain the bifurcated stent (200) in a contracted state. Resistance to expansion of the walls of the first tube, in particular in the bifurcated part (114), prevents expansion of the bifurcated stent, maintaining it in contracted state prior to deployment. After the bifurcated stent (200) is released from the first tube (102) through the slit (140, 140', 140"), the stent expands and occupies the bifurcated vessel lumen.

The bifurcated part (114) of the first tube (102) is provided with a slit (140, 140', 140"), configured for the passage of the bifurcated stent (200) therethrough. The slit connects the bifurcated parts of first lumen (134, 136) with an exterior of the first tube (102). The slit (140, 140', 140") may be radial with respect to a central axis of each limb. The bifurcated part of the first tube (102) releasably retains the bifurcated stent for deployment after the first (120) and second limbs (122) have been positioned within the bifurcation of the bodily vessel. The slit (140, 140', 140"), may be further configured for the passage of a guidewire therethrough.

Preferably the slit (140, 140', 140") extends from the first limb (120) to the second limb (122). More preferably, the slit extends in a proximal (20) direction from a distal (30) terminal end of the first limb (120) and in a proximal (20) direction from a distal terminal end of the second limb (122) and joins where the respective limbs (120, 122) are connected. The slit (140, 140', 140") may cross a central axis of the main part (112) of the first tube (102). The slit (140', 140") on each limb may be mutually facing. The slit (140', 140") may be straight and parallel with respect to a central axis of the corresponding limb, or inclined with respect to the central axis, or be partially helical. The slit may be continuous.

The slit (140, 140', 140") may be open or closed in a native state. Where it is closed, the slit edges are compliant to allow passage of the bifurcated stent therethrough. In the closed state, the slit edges may touch (e.g. FIG. 1, Panels B'-1, 142' and B-1, 142") or overlap (e.g. FIG. 1, Panels B'-2, 144' and B-2, 144").

Where the slit is open, the width of the slit may be adapted allow ease of passage by the bifurcated stent, while providing sufficient resistance to expansion of the walls to retain a self-expanding bifurcated stent in a closed state. The (140, 140', 140") slit may occupy a between 1-30% of the circumference of the limb (120, 122).

The slit (140, 140', 140") may be disposed with one or more breakable seals, configured to prevent passive passage of the bifurcated stent therethrough and/or to prevent expansion of a self-expanding bifurcated stent. The breakable seal may be broken as the delivery catheter (110) is withdrawn from the bifurcated stent (200) or as the bifurcated stent (200) is advanced using the pusher (500). The breakable seal may be formed by a region of reduced wall thickness of the first tube (102); the region of reduced wall thickness may span part of all of the slit. The breakable seal may be formed by a region where the slit is interrupted i.e. the edges of the slit are bridged by a non-cut part.

The slit may be formed by laser cutting, water cutting or milling of the wall of the first tube in the bifurcated part (114) which also allows formation of the breakable seal by, for instance, partial cutting to a certain depth and/or by providing the slit with interruptions (bridges).

The bifurcated part (114) of the first tube (102) is compliant and biased in an open (V-shaped) configuration. Upon the application of an external force, the bifurcated part (114) may transition into a folded configuration in which the respective distal ends of the first limb (120) and second limb (122) are brought closer together. With the release of the force, the bifurcated part (114) returns to the open (V-shaped) configuration. The foldable property allows slidable passage through a constricting lumen (330) of an access catheter (300). The bifurcated part (114) of the first tube (102) in the closed configuration is exemplified in FIG. 3 Panel A, and in the open configuration in FIG. 3. Panel C.

Controlled and gradual opening and/or folding of the bifurcated part (114) of the first tube may be actuated by a withdrawal of or advancement through a constricting second lumen (330) of an access catheter (300) described in more detail later below, namely sheathing or unsheathing of the bifurcated part (114) of the first tube. Preferably, the access catheter (300) is withdrawn while the first tube (102) is maintained in an essentially fixed relation to the site of treatment. Advantageously, the bifurcated part (114) of the first tube may be resheathed and repositioned where it has not been satisfactorily deployed or placed.

The first tube (102) may preferably be sized for slidable passage through, for example, the working channel of an endoscope or a second lumen of the second tube (described below). As a general guidance, for vascular applications, the maximum outer diameter of the main part (112) of the first tube (102) may be equal to or no greater than 0.1 F to 0.3 F (0.05 mm to 0.10 mm).

As a general guidance, the maximum diameter of the first lumen (132) of the main part (112) of the first tube (102) may be equal to or no greater than 0.1 F to 0.2 F (0.04 mm to 0.07 mm).

As a general guidance, the length of the main part (112) of the first tube (102) may be 120 to 160 cm, depending on the application. The respective diameters and length may be adapted according to the location with respect to the point of entry, dimensions of the vessel to be treated e.g. artery size, size of aneurism neck, and the anatomy.

The maximum outer diameter of the main part (112) of the first tube (102) may be greater than the maximum outer diameter of the first (120) and second (122) limbs. The maximum outer diameter of the first limb (120) may be the same or different from the maximum outer diameter of the second limb (122). The respective diameters may be adapted according to the dimensions of the vessel to be treated e.g. artery size, size of aneurism neck.

As a general guidance, for vascular applications (e.g. intracranial), the maximum outer diameter of the first (120) or second (122) limb of the first tube (102) may be equal to or no greater than 0.1 F to 0.2 F (0.04 mm to 0.07 mm).

As a general guidance, the maximum diameter of the first lumen (136, 134) of the first (120) or second (122) limb of the first tube (102) may be equal to or no greater than 0.09 F to 0.18 F (0.03 mm to 0.06 mm).

The length of the first limb (120) may be the same or different from the length of the second limb (122). The respective lengths may be adapted according to the dimensions of the vessel to be treated e.g. artery size, size of aneurism neck.

The lengths of the first limb (120) and the second limb (122) may be longer than the respective lengths of the first arm (220) and the second arm (222).

The first tube (102) may be formed using an extrusion process or non-extrusion process. A first tube may be formed from a biocompatible material which provides the requisite flexibility, pushability and strength. It may also exhibit low or no radial expansion. Suitable biocompatible materials include, but are not limited to a polymer such as polypropylene, polyethylene, polyurethanes, polyamide, polyimide poly(ethylene terephthalate) (PET) or polyesters and copolymers thereof, metal (stainless steel, NiTinol) of a combination of metal and polymer. In a preferred embodiment it is formed from a polymeric material that is polyamide, polyimide, stainless steel or NiTinol or a combination or blend of these. The first tube may be formed from a polymeric material (e.g. polyimide) strengthened with braided or coiled metal (stainless steel or NiTinol) disposed within the polyimide wall. For a first tube formed by extrusion, it is preferably formed from polyamide. For a first tube formed by non-extrusion, it is preferably formed from polyimide. The exterior may be coated to reduce friction during insertion or withdrawal. Example of a suitable friction-reducing coating includes Teflon.

The main part (112) of the first tube (102) may be provided with a coiled spring disposed at least partially along a length to increase stiffness and pushability, while maintaining flexibility. The coiled spring is preferably disposed adjacent to an inner wall of the first lumen. A rubber layer may be provided to protect the coiled spring. The rubber layer may be provided with a friction-reducing coating e.g. a hydrophilic polymers for ease of passage of a guidewire through the first lumen. It is an aspect that the bifurcated part of the first tube is devoid of the coiled spring; stiffness may be provided by the presence of the bifurcated stent.

The delivery catheter (110) may further be provided with one or more expandable balloons. The expandable balloon may be used for the treatment of an occlusion and/or for opening of the bifurcated stent that is balloon-expandable. The expandable balloon may be advanced towards the site of treatment via the first lumen (230) of the first tube (102). The expandable balloon and associated catheter may be slidable relative to the delivery catheter (110). In a particular example, an expandable balloon may be employed in order to perform intrastent angioplasty in case of non-full deployment of the bifurcated stent owing to anatomic complexity. The bifurcated stent may be mounted on balloons—one for each stent arm—that allows the deployment of a balloon-expandable stent.

The first tube (102) may comprise one or more additional lumens, for instance, for deployment of an expandable balloon, which may be used to perform in-stent angioplasty.

The treatment of arterial occlusion may be performed by 1) deploying the bifurcated stent through the clot (or thrombus), 2) pausing for a period in order to allow the clot to penetrate the struts of the bifurcated stent and 3) by pulling back (retrieving) the bifurcated stent with the clot that penetrated into its struts.

Figure 5:
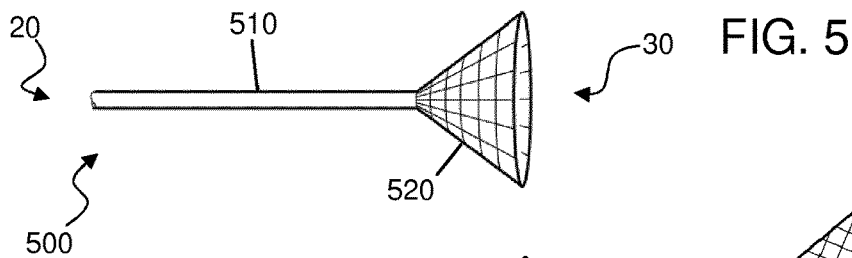
FIG. 5 depicts a pusher having a capture element in an open configuration.
Figure 6:
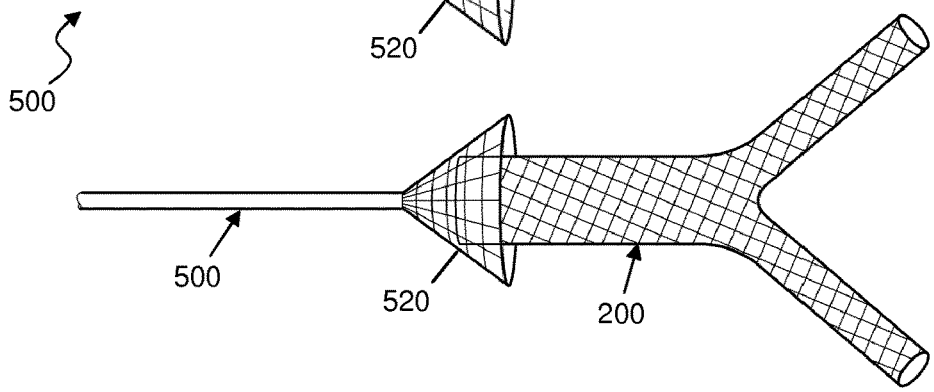
FIG. 6 depicts the pusher of FIG. 5 in abutting alignment with a bifurcated stent.

The delivery catheter (110) may further be provided with a flexible and slidable pusher (500) to assist with dispensing the bifurcated stent through the slit (140), as shown, for instance, in FIGS. 5 and 6. The pusher (500) comprises an elongated flexible rod (510) having a proximal (20) and distal (30) end, configured for passage through the first lumen (130) of the first tube (102). The pusher (500) may be slidable relative to the delivery catheter.

The pusher rod (510) may be formed from a biocompatible material which provides the requisite flexibility, pushability and strength. Suitable biocompatible materials include, but are not limited to a polymer such as polypropylene, polyethylene, polyurethanes, polyamide, polyimide poly(ethylene terephthalate) (PET) or polyesters and copolymers thereof. The rod exterior may be coated to reduce friction during passage through the first lumen (230) of the first tube (102). Examples of a suitable friction-reducing coating includes Teflon. The pusher rod may be formed from a hollow tube or may be at least partially, preferably fully solid.

According to one aspect, the distal end (30) of the pusher rod (500) may be permanently attached to the bifurcated stent (200) at its proximal end (20); for instance, when the bifurcated stent is used to treat a vascular occlusion by removal of a part of the occlusive material, there is no requirement for the bifurcated stent (200) to be released.

According to one aspect, the distal end (30) of the pusher rod (500) is provided with a capture element (520) for releasable attachment to the bifurcated stent (200) at its proximal end (20). The capture element (520) may be provided in fixed slidable and preferably rotational relation with the distal end of the pusher rod. The capture element (520) may be radially self-expanding e.g. a radially self-expanding claw or net that may adopt an open or folded configuration. The folded configuration is for passage within the first lumen (130) of the first tube (102) wherein the peripheral edges of the capture element (520) are closer together, typically having an essentially "I"-shaped profile. The capture element (520) in the folded configuration is able to grip the proximal end (20) of the bifurcated stent (200); once gripped, translations and preferably rotations of the pusher rod are transferred to the bifurcated stent (200). The open configuration is adopted after deployment of the bifurcated stent (200) the peripheral edges being disposed wider apart, typically having an essentially conical or dome-shaped form. The capture element (520) in the open configuration releases the grip of the proximal end (20) of the bifurcated stent (200).

The capture element (520) may be compliant and biased in the open (conical or dome-shaped-shaped) configuration. Upon the application of radial force the capture element (520) transitions into the folded configuration. The capture element (520) may be retained in the closed ("I"-shaped profile) configuration within the first lumen (130) of the first tube (102). With the release of the radial force, the capture element (520) returns to the open configuration. The capture element (520) may adopt the open configuration after it has been advanced through the slit (140) of the bifurcated part (114) of the first tube. The capture element (520) in the closed configuration is exemplified in FIGS. 7A to C, and in the open configuration in FIGS. 5 and 6.

Advancement of the pusher (500) in a distal (30) direction while the position of the delivery catheter (110) is maintained, or withdrawal of the delivery catheter (110) while the position of the pusher (500) is maintained allows the bifurcated stent (200) to be deployed i.e. ejected from the slit. FIG. 9, Panels A and B, depict a sequence where the pusher (500) is maintained at a constant position while the delivery catheter (110) is withdrawn proximally, thereby deploying the bifurcated stent (200).

Figure 7A:
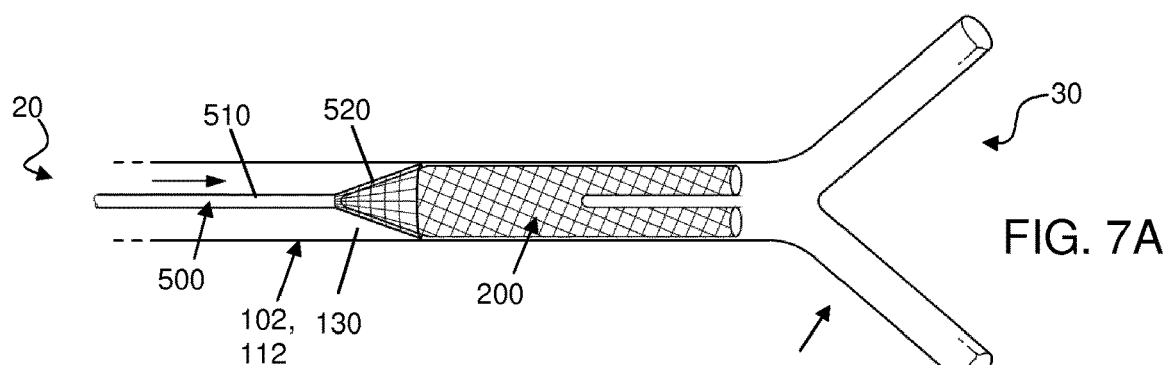
FIGS. 7A to 7C depict a loading sequence for loading a bifurcated stent into the limbs of a delivery catheter.
Figure 7B:
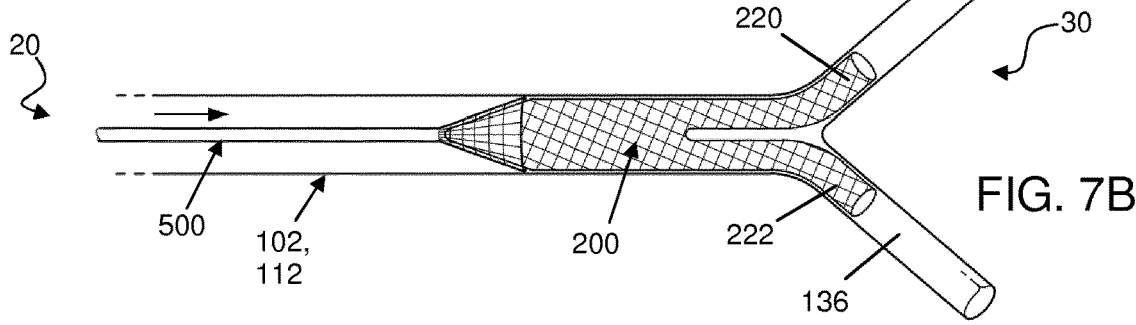
Figure 7C:
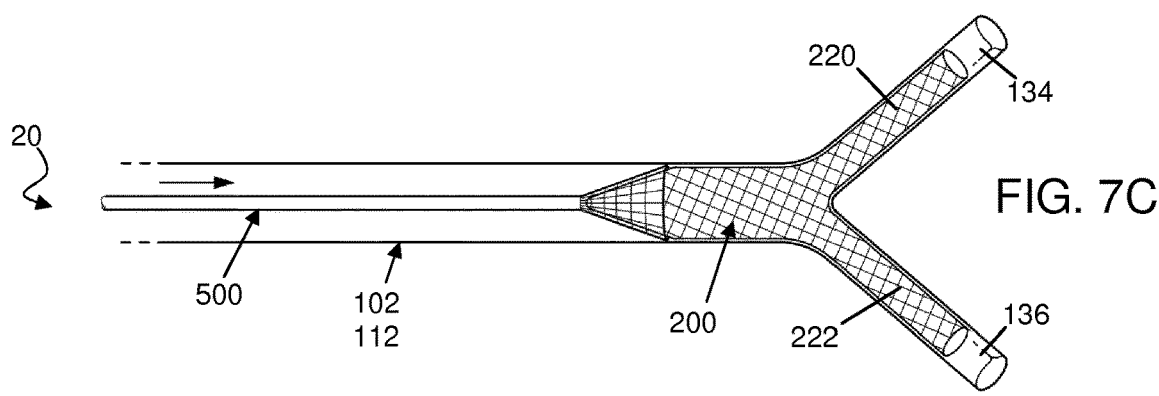

It is noted that the pusher (500) may be utilized for loading the bifurcated stent (200) into the limbs (120, 122) of the delivery catheter (110). A loading sequence is depicted, for instance, FIGS. 7A to 7C. In the folded configuration, the bifurcated stent (200) may be introduced into the proximal end (20) of the first lumen (130) of the main part (112) of the first tube (102), where, being gripped by the capture element (520) in the closed configuration, it is advanced in a distal (30) direction along first lumen (130) of the main part (112) as shown in FIG. 7A. Where it reaches the bifurcated part (114) of the first tube (102), the bifurcated stent (200) arms (220, 222) unfold into and occupy the lumen (134, 136) in the bifurcated part (114) of the first tube (102) (FIGS. 7B and 7C). It is appreciated that loading of the bifurcated stent (200) into the delivery catheter (110) may be performed over a pair of guidewires.

Figure 3:
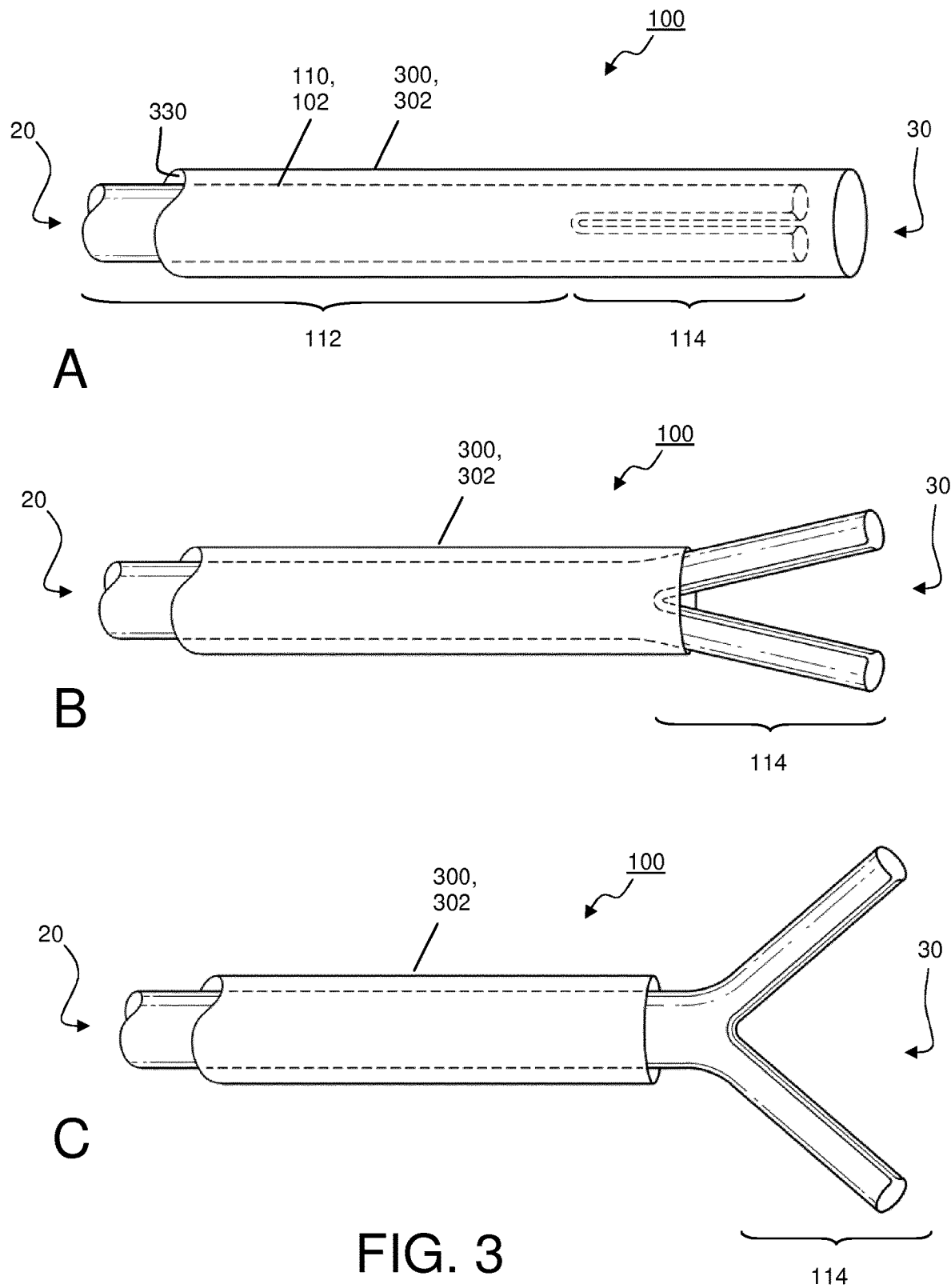

The delivery system (100) for the bifurcated stent may further comprise an access catheter (300) for delivering the delivery catheter (110) to the site of treatment, as shown, for instance in FIG. 3 Panels A to C.

The access catheter (300) comprises an elongated second tube (302) having a proximal end (20) and a distal end (30) provided with a second lumen (330) adapted to slidably accommodate the delivery catheter (110) or first tube (102). The second tube (302) is configured to slidably accommodate the bifurcated part (114) of the first tube (102) in a folded configuration.

The proximal (20) and distal (30) terminal ends of the second tube (302) are open. The second tube (302) may be cylindrical, having a generally uniform outer shape in the proximal region. It will be appreciated that an open proximal end may be configured for connection to one or more hubs. One or more hubs such as a Y-type connector, optionally with Luer fittings may be fitted to the proximal terminal end of the access catheter or second tube to facilitate passage of the first tube or delivery catheter, guidewire, equipment to provide torque/longitudinal force via the first tube.

As would be understood by those of skill in the art, the second tube (302) may preferably be sized for slidable passage through, for example, the working channel of an endoscope or through a body lumen, in particular vasculature (through an introducer). As a general guidance, for vascular applications (e.g. intracranial), the maximum outer diameter of the second tube (302) towards the distal (in situ) end may be equal to or no greater than 4 F to 6 F (1.33 mm to 2 mm).

As a general guidance, the maximum diameter of the second lumen (330) the distal (in situ) end may be equal to or no greater than 3.9 F to 5.9 F (1.30 mm to 1.97 mm).

As a general guidance, the length of the second tube (302) may be 110 to 150 cm, depending on the application.

The second tube (302) may be formed using an extrusion process or non-extrusion process. A second tube (302) may be formed from a biocompatible material which provides the requisite flexibility, pushability and strength. Suitable biocompatible materials include, but are not limited to a polymer such as polypropylene, polyethylene, polyurethanes, polyamide, polyimide poly(ethylene terephthalate) (PET) or polyesters and copolymers thereof, metal (stainless steel, NiTinol) of a combination of metal and polymer. In a preferred embodiment it is formed from a polymeric material that is polyamide, polyimide, stainless steel or NiTinol or a combination or blend of these. The second tube (302) may be formed from a polymeric material (e.g. polyimide) strengthened with braided or coiled metal (stainless steel or NiTinol) disposed within the polyimide wall. For a second tube (302) formed by extrusion, it is preferably formed from polyamide. For a second tube (302) formed by non-extrusion, it is preferably formed from polyimide. The exterior may be coated to reduce friction during insertion or withdrawal. Example of a suitable friction-reducing coating includes Teflon.

The second tube (302) may be provided with a coiled spring disposed at least partially along a length to increase stiffness and pushability, while marinating flexibility. The coiled spring is preferably disposed adjacent to an inner wall of the second lumen. A rubber layer may be provided to protect the coiled spring. The rubber layer may be provided with a friction-reducing coating e.g. a hydrophilic polymers for ease of passage of the first tube through the second lumen.

The second tube (302) may comprise one or more additional lumens, for instance, for deployment of an expandable balloon for the treatment of an occlusion.

Figure 8:
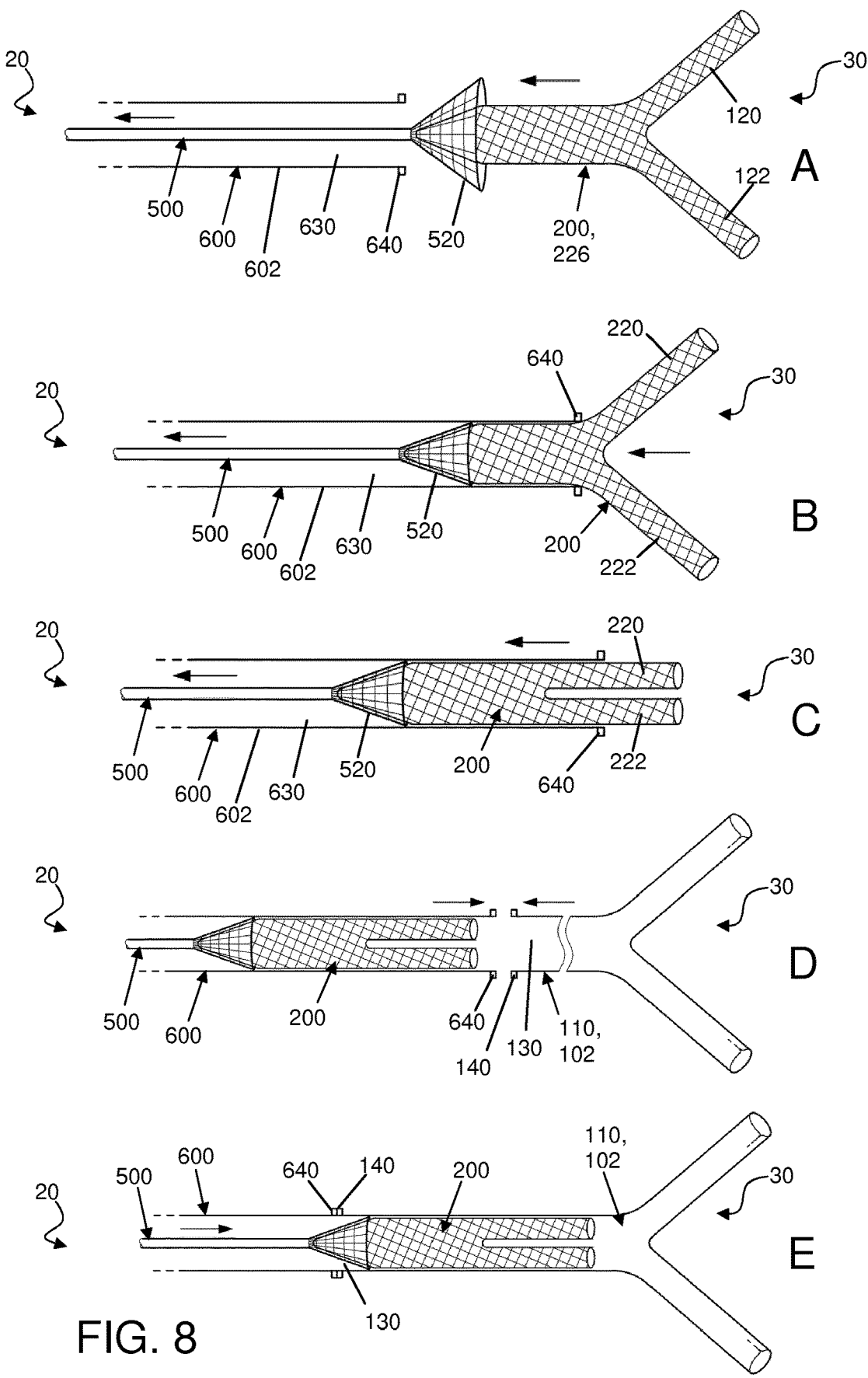
FIGS. 8A to 8E depict a loading sequence for loading a bifurcated stent a first lumen of delivery catheter.

The delivery system (100) may further comprise a loader (600) configured for loading of the bifurcated stent (200) into the delivery catheter (110), as shown, for instance in FIG. 8 Panels A to E.

The loader (600) comprises an elongated third tube (602) having a proximal end (20) and a distal end (30) provided with a third lumen (630) adapted to slidably accommodate the bifurcated stent (200) in the folded configuration.

The distal end (30) of the third tube (602) is configured to couple with the proximal terminal end of the delivery catheter (110) such that the first (130) and third (630) lumens are connected to form a continuous passage for advancement of the bifurcated stent (200) in the folded state from the loader (600) to the delivery catheter (110). The proximal (20) and distal (30) terminal ends of the third tube (602) are open. The distal end (30) of the third tube (602) may be provided with a coupling (640) (e.g. a Luer filling, a push connector, a narrowed region of the third tube (602)) configured to connect with a complementary coupling (140) provided on the proximal end of the first tube (102) such as a hub.

The third tube (602) may be cylindrical, having a generally uniform outer shape in the distal region.

The proximal end (stem part (226)) of the bifurcated stent (200) is inserted into the distal end of the third (630) lumen, and the bifurcated stent (200) withdrawn proximally (20) so as to fold the arms (220, 222) as the third tube (602) covers them (FIG. 8, Panels A to C).

Subsequently, the distal end (30) of the third tube (602) is coupled to the proximal end of the first tube (102) such that the respective lumens (630, 130) form a continuous passage (FIG. 8, Panel D). Subsequently, the bifurcated stent (200) is advanced distally (30) such that it enters the first lumen (130) of the first tube (102) (FIG. 8, Panel E). The loader (600) thus facilitates loading of the bifurcated stent (200) from the proximal end of the delivery catheter (110) wherein the arms (120, 122) are oriented in a distal (30) direction.

It is appreciated that the pusher (500) or other type of rod may be used to advance and withdrawal of the bifurcated stent (200) relative to the loader (600).

The delivery system (100) may be provided with at least one guidewire, preferably two guidewires. The guidewire may have a shapeable distal end for intraluminal navigation.

There are two main types of catheter in common use—rapid exchange (monorail) and over the wire (OTW). Over the wire catheters employ a long guidewire lumen from the proximal end to the distal end of the catheter. Rapid exchange catheters employ a distal guidewire lumen, having a side port for exits of the guidewire towards the distal end. The fact that the guidewire is received only within a distal portion allows the catheter to be readily exchanged without the need for guidewire extenders or for an excessively long guidewire. The present delivery system can be readily adapted for guidewire deployment using either mode. The figures demonstrate an OTW mode, however, it is readily within the competence of the skilled person to adapt it for the rapid exchange mode of operation.

The delivery system (100) may comprise the delivery catheter (110) and one or more of the following elements:
the bifurcated stent (200),
the access catheter (300),
one or more, preferably 2 guidewires.

The delivery system (100) may be provided as a kit comprising the delivery catheter (110) and one or more of the following elements:
the bifurcated stent (200),
the access catheter (300), one or more, preferably 2 guidewires.

The delivery system (100) may comprise the delivery catheter (110) and one or more of the following elements:
- the bifurcated stent (200),
- the access catheter (300),
- the pusher (500),
- the loader (600), and
- one or more, preferably 2 guidewires.

The delivery system (100) may be provided as a kit comprising the delivery catheter (110) and one or more of the following elements:
- the bifurcated stent (200),
- the access catheter (300),
- the pusher (500),
- the loader (600), and
- one or more, preferably 2 guidewires.

It is appreciated that the delivery system (100) or kit may be supplied wherein the delivery catheter (110) and one or more of the elements are not co-assembled.

A further aspect described herein relates to a method for delivery of a bifurcated stent to a site of treatment using the delivery system (100) described herein comprising:
- advancing intravascularly the access catheter (300) disposed with the delivery catheter (110) loaded with the bifurcated stent (200) to the site of treatment through the access catheter (300),
- opening gradually the delivery catheter (110) by withdrawal of the access catheter (300), and
- deploying the bifurcated stent (200) through the slit (140) by withdrawal of the delivery catheter (110).

The delivery system (100) may be advanced intravascularly along one or more, preferably a pair of guidewires. Typically, there is one guidewire per arterial branch. Guidewire placement precedes advancement of the delivery system (100).

Further aspect described herein relates to a method for treatment of an arterial aneurism located at a vessel bifurcation using the delivery system (100) described herein comprising:
- advancing intravascularly the delivery catheter (110) loaded with the bifurcated stent (200) to the site of the aneurism through the access catheter (300),
- opening gradually the delivery catheter (110) by withdrawal of the access catheter (300) such that each limb (120, 122) of the delivery catheter (110) is positioned within a branch of the vessel bifurcation, and
- deploying the bifurcated stent (200) through the slit by withdrawal of the delivery catheter (110), such that each arm (220, 222) of the bifurcated stent (200) is positioned within a branch of the vessel bifurcation.

After deployment, the bifurcated stent (200) is detached from the delivery system (100), for instance, from the pusher (500), and bifurcated stent (200) remains in situ.

Further aspect described herein relates to a method for treatment of an arterial occlusion located at a vessel bifurcation using the delivery system (100) described herein comprising:
- advancing intravascularly the delivery catheter (110) loaded with the bifurcated stent (200) to the site of the occlusion through the access catheter (300),
- opening gradually the delivery catheter (100) by withdrawal of the access catheter (300) such that each limb (120, 122) of the delivery catheter (110) is positioned within a branch of the vessel bifurcation,
- deploying the bifurcated stent (200) through the slit (140) by withdrawal of the delivery catheter (110), such that each arm (220, 222) of the bifurcated stent (200) is positioned within a branch of the vessel bifurcation and one or both arms (220, 222) are positioned within occlusive material (e.g. clot, thrombus, emboli),
- withdrawing bifurcated stent (200) together with at least part of the occlusive material.

Withdrawal of the bifurcated stent (200) may be effected by a pusher rod attached to the bifurcated stent (200).

The arterial aneurism or arterial occlusion may be intracranial.

Further aspect described herein relates to a method for loading bifurcated stent (200) into the delivery catheter (110) comprising the steps:
- inserting the proximal end (20) of the bifurcated stent (200) the distal end of the distal end (30) of the third (630) lumen of the loader (600),
- withdrawing the bifurcated stent (200) proximally (20) so as to fold the arms (120, 122) as the third tube (602) covers them,
- coupling the distal end (30) of the third tube (602) to the proximal end of the first tube (102) delivery catheter (110) of the such that the respective lumens (630, 130) form a continuous passage.
- advancing the bifurcated stent (200) distally (30) such that it enters the first lumen (130) of the first tube (102).

By use of the method, the bifurcated stent (200) is loaded the proximal end of the delivery catheter (110) and the arms (120, 122) are oriented in a distal (30) direction for subsequent deployment. The method may employ a pusher (500) to advance or withdraw the bifurcated stent (200) relative to the loader (600).

FIGURES

FIG. 1 depicts a delivery catheter (110) in an open configuration having a proximal (20) and distal end (30) comprising a first tube (102) disposed with a first lumen (130, 132, 134, 136). The first tube (102) is bifurcated at the distal end (30) at a bifurcation point (124), forming a proximal main part (112) disposed with the first lumen (132) and bifurcated part (114) where the first lumen (134, 136) advances into each of the limbs (120, 122) of the bifurcated part (114). The bifurcated part (114) is disposed with a longitudinal slit (140) for passage of the bifurcated stent (200).

FIG. 1 panel B and B' illustrate a transverse cross section through the first limb (120) and second limb (122) respectively, together with the respective slits (140', 140") and the respective parts of the first lumen (134, 136). Panel A illustrates a transverse cross section through the main part (112) of the first tube (102).

FIG. 2 depicts a bifurcated stent (200) in an open (Y) configuration having a proximal (20) and distal (30) end and comprising a stem part (226) at the proximal end (20) bifurcating at a bifurcation point (224) into a pair of arms (220, 222) at the distal end (30). A stent lumen (230) extends from the proximal end (232) of the stem part (226) to the distal end of each arm (234, 236).

FIG. 3 panels A to C each depict an access catheter (300) having a proximal (20) and distal (30) end comprising a second tube (302) disposed with a second lumen (330), wherein the second lumen (330) slidably accommodates the first tube (102). In Panel A, the bifurcated part (114) of the first tube (102) is fully withdrawn within the second lumen (330) causing the bifurcated part (114) to adopt the folded configuration. In Panel B, the bifurcated part (114) of the first tube (102) is partially withdrawn within the second lumen (330) causing the bifurcated part (114) to adopt an open configuration. In Panel C, the bifurcated part (114) of the first tube (102) is fully unsheathed from the second lumen (330) allowing the bifurcated part (114) to adopt a fully open configuration.

Figure 4:
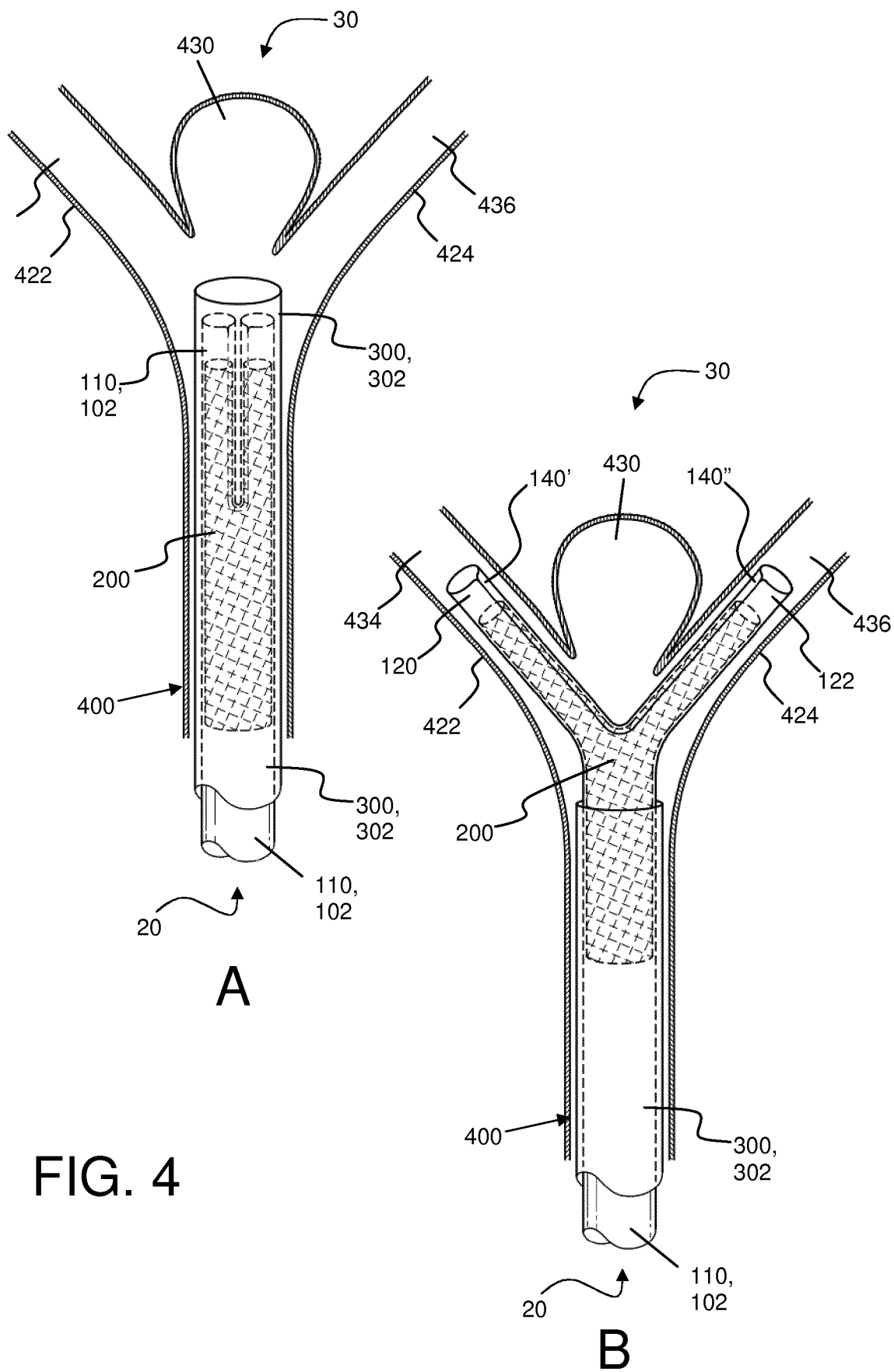
Figure 4:
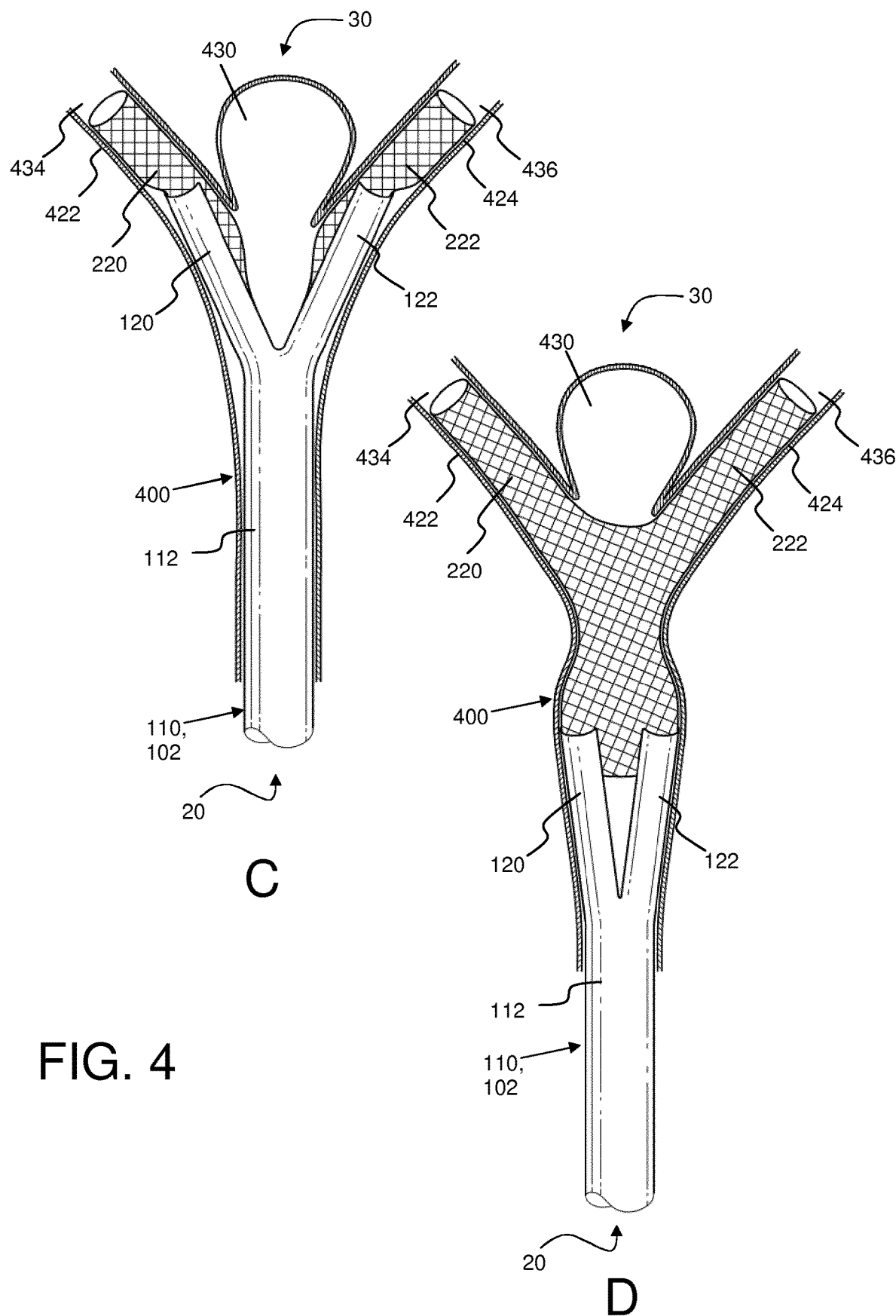

FIG. 4 panels A to D show a delivery and deployment sequence into a portion of an artery (400) having proximal (20) and (30) distal end that is a bifurcated at the distal end (30) into two branches (422, 424) which lead off from a main part (426) of the artery. An arterial lumen (430) has a corresponding lumen main part (432) and lumen branches (434, 436). An abnormality that is aneurism sac (430) has formed where the branches (422, 424) bifurcate. In Panel A, the delivery system (100) has been advanced along the main part (426) of the artery and proximal to the bifurcated part of the artery (400). The delivery system (100) comprises a bifurcated stent (200) loaded into the bifurcated part of the delivery catheter (110), and an access catheter (300) into which the delivery catheter (110) is withdrawn to maintain the limbs in a folded configuration. Typically the delivery system (100) is advanced along two guidewires (not shown), one guidewire for each arm of the bifurcated stent and threaded through each of the arterial braches. In Panel B, the access catheter (300) has been withdrawn relative to the delivery catheter (110), thereby unsheathing the delivery catheter (110) and opening the limbs (120, 122), each of which has been positioned into a branch (422, 424) lumen (434, 436) of the bifurcated artery (400). In practice, the unsheathing is done gradually and in tandem with positioning. The delivery catheter (110) may be repeatedly re-sheathed and un-sheathed for optimum placement. In Panel C, the delivery catheter (110) has been partially withdrawn relative to the bifurcated stent (200), thereby partly dispensing the bifurcated stent (200) through the slit (140).

Each arm (220, 222) of the bifurcated stent (200) is disposed into a branch (422, 424) lumen (434, 436) of the bifurcated artery (400). Guidewires where used are preferably immobilised during dispensing. In Panel D, the delivery catheter (110) has been further withdrawn relative to the bifurcated stent (200). Each arm (220, 222) of the bifurcated stent (200) is fully deployed into an arterial branch (422, 424) lumen (434, 436), and the stem (226) is partially deployed. The stent mesh covers the wide neck of the aneurism sac (430).

FIG. 5 depicts a pusher (500) having a proximal (20) and distal (30) end comprising an elongated flexible rod (510) disposed at the distal end (30) with a capture element (520) in an open configuration for releasable attachment to the bifurcated stent (200) at its proximal end (20).

FIG. 6 depicts the pusher (500) of FIG. 5 where the capture element (520) in an open configuration is in abutting relation to the bifurcated stent (200), and prior to capture.

FIGS. 7A to 7C depict a loading sequence for loading the bifurcated stent (200) into the limbs (120, 122) of the delivery catheter (110). In FIG. 7A, the bifurcated stent (200) in a folded configuration is gripped by the capture element (520) in the closed configuration and advanced in a distal (30) direction along first lumen (130) of the main part (112) of the first tube (102) by pushing the elongated flexible rod (510) in a distal direction. In FIG. 7B, the bifurcated stent (200) arms (220, 222) start to unfold into and occupy the lumen (134, 136) in the bifurcated part (114) of the first tube (102). In FIG. 7C, the bifurcated stent (200) is fully loaded into the bifurcated part (114) of the first tube (102).

FIG. 8, Panels A to E depict a loading sequence for loading the bifurcated stent (200) into the delivery catheter (110) such that the arms (220, 222) are aligned in a distal direction. The proximal end (stem part (226)) of the bifurcated stent (200) is inserted into a capture element (520) of the pusher (500) in the open configuration (Panel A). The pusher (500) is withdrawn proximally (20) into the distal end of the third (630) lumen so as to fold the capture element (520) and grip the stem part (226) of the bifurcated stent (200) (Panel B). The pusher (500) is further withdrawn proximally (20) so as to fold the bifurcated stent (200) arms (220, 222) as the third tube (602) covers them (FIG. 8, Panels A to C). After the bifurcated stent (200) arms (220, 222) have been closed, the distal end (30) of the third tube (602) is coupled via a coupling (640) to the proximal end of the first tube (102) disposed with a complementary coupling (140) such that the respective lumens (630, 130) form a continuous passage (FIG. 8, Panel D). Subsequently, the bifurcated stent (200) is advanced distally (30) by pushing the pusher (500) forward such that bifurcated stent (200) enters the first lumen (130) of the first tube (102) (FIG. 8, Panel E).

FIG. 9, panels A and B show a deployment sequence into a portion of an artery (400) akin to the sequence shown in FIG. 4, wherein the bifurcated stent (200) is maintained or advance reactive to the delivery catheter (110) using the pusher (500). In Panel A, the limbs (120, 122) of the delivery catheter (110) have been positioned into a branch (422, 424) lumen (434, 436) of the bifurcated artery (400). The delivery catheter (110) has been partially withdrawn relative to the bifurcated stent (200) which is maintained in position maintaining the pusher rod (500) fixed relative to the site of treatment, thereby partly dispensing the bifurcated stent (200) through the slit (140). In Panel B, the delivery catheter (110) has been further withdrawn relative to the pusher rod (500) and bifurcated stent (200). Each arm (220, 222) of the bifurcated stent (200) is fully deployed into an arterial branch (422, 424) lumen (434, 436), and the stem (226) is partially deployed. The stent mesh covers the wide neck of the aneurism sac (430).

FIG. 10, panels A to H show different bifurcated stent (200) configurations according to the dimension of the arterial branches (422, 424). Compared with Panel A, in Panels B and C, the length of the bifurcated stent arms are different; in Panel D, the length of the bifurcated stent stem is different; in Panel E, the branch angle is different as is the diameter of the left branch of the bifurcated stent; in Panel F, the branch angle is different as is the diameter of the right branch of the bifurcated stent; in Panel G, the branch angle is different, as are the diameters and length of the branches. In Panel H, similar to panel G, the porosity of the right stent branch varies at region 224'.

The invention claimed is:

1. A delivery system for a bifurcated stent having a stem and a pair of arms, the delivery system comprising:
   a delivery catheter comprising an elongated first tube having a proximal end and a distal end, and a tubular bifurcated part at the distal end configured to accommodate and radially constrain the arms,
   wherein the tubular bifurcated part includes tubular lumens,
   wherein a longitudinal slit disposed on the tubular bifurcated part, including the tubular lumens, is configured for releasable passage of the bifurcated stent therethrough,
   wherein the slit edges are apart or touch,
   wherein the slit spans no more than 30% of a circumference of each of the lumens while the slit is closed, and wherein the tubular bifurcated part is formed of a compliant material configured to resists expansion of the bifurcated stent, and allow repeatable opening and closing of the slit.

2. The delivery system according to claim 1, wherein the longitudinal slit extends from a first limb to a second limb of the tubular bifurcated part.

3. The delivery system according to claim 1, wherein the tubular bifurcated part of the first tube comprises a first and second limb each configured for passage through a branch of a bifurcated bodily vessel.

4. The delivery system according to claim 3, wherein the first and second limbs are each configured to compress radially the bifurcated stent.

5. The delivery system according to claim 1, further comprising an access catheter comprising an elongated second tube having a proximal end and a distal end provided with a second lumen adapted to slidably accommodate the first tube, and configured to control a gradual opening or folding of the tubular bifurcated part of the first tube responsive to slidable relative displacement of the first and second tubes.

6. The delivery system according to claim 5 wherein the delivery catheter is configured for an over-the-wire or rapid exchange mode of operation.

7. The delivery system according to claim 1, further comprising the bifurcated stent that is self-expanding.

8. The delivery system according to claim 7, wherein the bifurcated stent is provided with an elutable active pharmaceutical ingredient.

9. The delivery system according to claim 7, wherein the bifurcated stent is prepared by laser cutting or braiding.

10. The delivery system according to claim 1, further comprising a pusher comprising an elongated flexible rod having a proximal and distal end, and a capture element at the distal end for releasable attachment to the bifurcated stent at its proximal end which capture element is radially self-expanding to adopt an open or folded configuration, wherein the folded configuration is configured for passage within a first lumen of the first tube and peripheral edges of the capture element are closer together to grip the proximal end of the bifurcated stent, and wherein the open configuration is configured for release of the bifurcated stent.

11. The delivery system according to claim 1, further comprising a loader for loading of the bifurcated stent into the delivery catheter comprising an elongated third tube having a proximal end and a distal end provided with a third lumen adapted to slidably accommodate the bifurcated stent in a folded configuration, wherein the distal end of the third tube is configured to couple with the proximal end of the delivery catheter such that a first lumen of the delivery catheter and the third lumen are connected to form a continuous passage for advancement of the bifurcated stent in the folded configuration from the loader to the delivery catheter.

12. The delivery system of claim 1, wherein the tubular lumens are joined at a joint and spread apart as the tubular members extend away from the distal end of the first tube.

13. The delivery system of claim 12, wherein the slit extends through the joint and along entire lengths of the tubular lumens.

14. A kit comprising the delivery catheter as defined in claim 1, and one or more of:
an access catheter,
a pusher,
a loader, and
one or more guidewires.

15. A method for delivery of a bifurcated stent to a site of treatment using the delivery system as defined in claim 1 comprising the steps:
advancing intravascularly the delivery catheter loaded with the bifurcated stent to the site of treatment through an access catheter,
opening gradually the delivery catheter by withdrawal of the access catheter, and
deploying the bifurcated stent through the slit by withdrawal of the delivery catheter.

16. The method according to claim 15, for treatment of an arterial aneurism or arterial occlusion.

17. A delivery assembly comprising:
a bifurcated stent including a stem and first arms;
a delivery catheter comprising an elongated first tube having a proximal end and a distal end, and a tubular bifurcated part proximate the distal end of the first tube, wherein the tubular bifurcated part includes second tubular arms configured to receive within the second tubular arms the first arms of the bifurcated stent, and the tubular bifurcated part is formed of a complaint material; and
a slit formed by slit edges in the tubular bifurcated part extends longitudinally along the tubular bifurcated part including the second tubular arms, the slit edges are biased towards each other by the complaint material as the slit edges move relative to each other to open and close the slit, and the slit spans no more than 30% of a circumference of each of the first and second tubular arms while the slit is closed;
wherein the complaint material applies a bias to the bifurcated stent resisting expansion of the bifurcated stent.

18. The delivery assembly of claim 17, wherein the slit edges are always detached from each other.

19. The delivery assembly of claim 17, wherein the second tubular arms are joined at a joint and spread apart as the second tubular arms extend away from the distal end of the first tube.

20. The delivery assembly of claim 19, wherein the slit extends through the joint and along entire lengths of the second tubular arms.

* * * * *